(12) United States Patent
Rolla

(10) Patent No.: US 8,517,736 B2
(45) Date of Patent: Aug. 27, 2013

(54) METHOD FOR ALLEVIATING THE UNDESIRED SIDE EFFECTS OF DENTAL BLEACHING

(75) Inventor: Gunnar Rolla, Oslo (NO)

(73) Assignee: Dr. Gunnar Rolla Consultant AS, Oslo (NO)

( * ) Notice: Subject to any disclaimer, the term of this patent is extended or adjusted under 35 U.S.C. 154(b) by 0 days.

(21) Appl. No.: 13/347,003

(22) Filed: Jan. 10, 2012

(65) Prior Publication Data

US 2012/0213716 A1    Aug. 23, 2012

(30) Foreign Application Priority Data

Feb. 23, 2011  (NO) .................................... 20110300

(51) Int. Cl.
  *A61K 8/19*   (2006.01)
  *A61K 8/21*   (2006.01)
  *A61K 8/22*   (2006.01)
  *A61Q 11/00*  (2006.01)

(52) U.S. Cl.
  USPC ............. 433/215; 424/52; 424/682; 424/688; 424/693

(58) Field of Classification Search
  USPC .............................. 206/570; 424/52; 433/215
  See application file for complete search history.

(56) References Cited

U.S. PATENT DOCUMENTS

| | | | | |
|---|---|---|---|---|
| 5,880,076 A | * | 3/1999 | Vermeer | 510/123 |
| 7,458,464 B1 | * | 12/2008 | Kutsch et al. | 206/570 |
| 2007/0218018 A1 | | 9/2007 | MacDonald | |
| 2008/0213197 A1 | * | 9/2008 | Busch et al. | 424/52 |

FOREIGN PATENT DOCUMENTS

WO    2006/073559    7/2006

OTHER PUBLICATIONS

Attin et al., "Effect of fluoride treatment on remineralization of bleached enamel." Journal of Oral Rehabilitation, 1997:24(4);282-286.*
Efeoglu et al., "Thirty-five percent carbamide peroxide application causes in vitro demineralization." Dental Materials 2007:23;900-904.*
Foreman et al., "A review of calcium hydroxide." International endodontic Journal 1990:23;283-297.*
Fuss et al., "Tubular Permeability to Calcium Hydroxide and to Bleaching Agents." Journal of Endodontics 1989:15(8);362-364.*
Travess et al., "Orthodontics. Part 6: Risks in orthordontic treatment." British Dental Journal 2004:196(2);71-77.*
M. Giniger et al., "A 180-Day Clinical Investigation of the Tooth Whitening Efficacy of a Bleaching Gel with Added Amorphous Calcium Phosphate", The Journal of Clinical Dentistry, vol. 16, No. 1, pp. 11-16, 2005.

* cited by examiner

*Primary Examiner* — Walter Webb
(74) *Attorney, Agent, or Firm* — Wenderoth, Lind & Ponack, L.L.P.

(57) ABSTRACT

The present invention relates to a method for reducing or eliminating loss of minerals from the enamel and dental hypersensitivity against temperature changes, in particular when caused by the bleaching of teeth with products containing hydrogen peroxide or other oxidizing agents. After the bleaching process the teeth are treated with a calcium hydroxide containing solution, and subsequently the teeth are treated with a fluoride solution.

8 Claims, 2 Drawing Sheets

METHOD FOR ALLEVIATING THE UNDESIRED SIDE EFFECTS OF DENTAL BLEACHING

Figure 1:
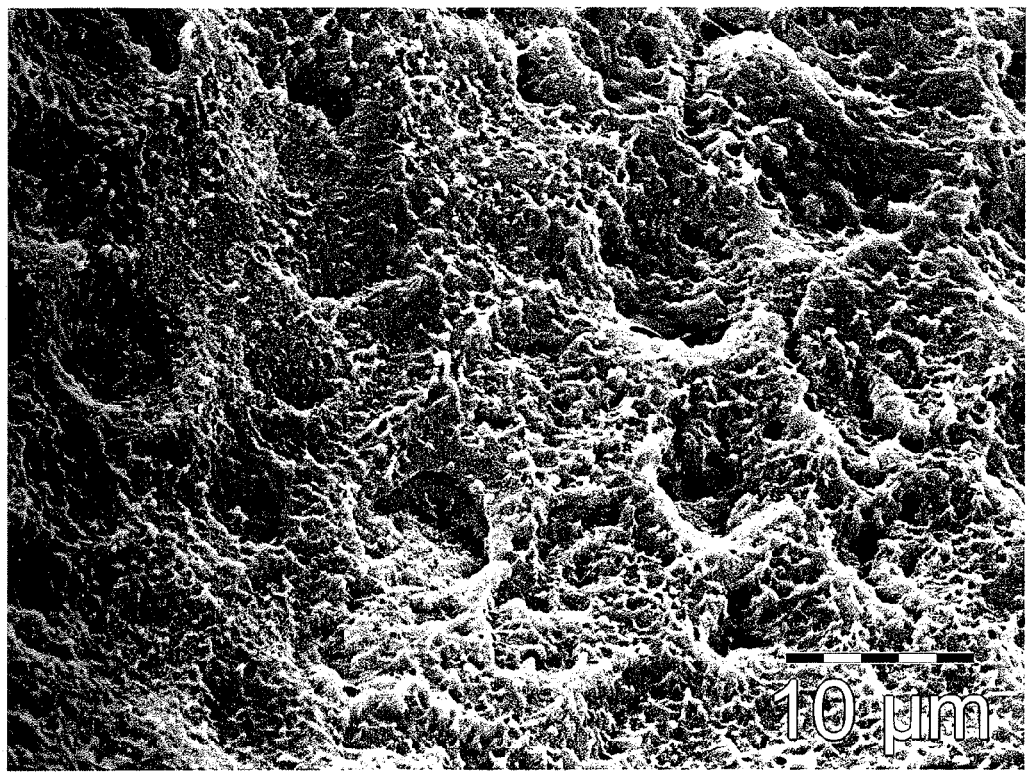

The present invention relates to a method for alleviating the undesired side effects of dental bleaching.

Dental bleaching is the cheapest form of cosmetic dentistry and is universally accepted by young people of both sexes. It has been estimated that 15% of the population of USA has tried dental bleaching, and that almost everybody testing bleaching for the first time experienced a subjective feeling of having a "whiter" smile and probably a slightly increased self confidence, judged to be important in a competitive world. Not only actors, television stars and business people in "public relations" need such smiles, but also ordinary young and not quite so young, people all over the world.

However, it is established beyond doubt that the bleaching procedures, which all are based on the strong oxidizing agent hydrogen peroxide, exhibit unfortunate side effects. Hypersensitivity of bleached teeth to temperature changes and to mechanical trauma such as tooth brushing is frequently associated with dental bleaching. It has been reported in many research publications that bleached teeth also exhibit pitted and porous surfaces, which will facilitate future "discolouration", and thus, reduce the time to the next "maintenance bleaching". In most cases this is necessary to keep the original bleaching level.

The mechanisms involved in the sensitizing of bleached teeth are not known, and so far no effective treatment is available. The good news is that the pain will not last forever, but will eventually disappear after some weeks (or some months). It may be a comfort for the ordinary patients, suffering from hypersensitive teeth, that they share this problem with film stars.

Fluoride application does not seem to affect the development of hypersensitivity after bleaching, as almost everybody is exposed to this element in the drinking water (in USA), or in fluoridated toothpaste, everywhere else. Some people believe that carbamide peroxide produce less side effects than hydrogen peroxide. However, peroxide is the effective part of both these compounds. Carbamide peroxide is used in some cases because it assumed to be more stable during storage.

The present invention relates to a method for reducing the undesired side effects associated with tooth bleaching, as described above. A simple and inexpensive method is provided, by which the symptoms are alleviated or eliminated, and the teeth restored to their original condition.

A newly erupted tooth has usually a smooth enamel surface, which is shining white. The enamel covers the dentin, which is softer and has a yellowish colour. Enamel consists of a biological apatite, which contains mineral contaminations in addition to the usual calcium and phosphate, and is therefore softer and more soluble than chemically pure hydroxyapatite. The enamel contains crystal rods which are densely packed and very hard. It also contains small amounts of phosphoproteins (enamelins) which glue the crystal rods together. The enamelins also serve essential functions during tooth development, before the eruption. The quality of the newly erupted teeth depends on the quality of the diet received during childhood, but also on hereditary factors. Sufficient amounts of calcium, phosphate and vitamin D are essential. Thus, the quality of the enamel is not necessarily similar for different people. The teeth are getting more yellow over time. A person with a strong, well mineralized enamel, exhibits an acceptable tooth colour longer, than a person with a porous and pitted tooth surface, maybe due to insufficient diet during childhood. The yellowish tooth colour originates often because the yellowish dentin is visible through insufficiently mineralized enamel.

The chemical properties of hydroxyapatite of the enamel are fairly well known, as this material was used for column chromatography in the past. It was shown that acidic macromolecules were bound to hydroxyapatite, and could be eluted by a gradient of phosphate. This indicated that the acidic macromolecules are in fact bound to calcium sites on the enamel surface. Albumin was often used as a model of an acidic macromolecule in these experiments. Under different conditions it was also possible to bind basic macromolecules to the hydroxyapatite surface. In this case the basic macromolecules (lysozymes) were eluted with a calcium gradient, indicating that the basic lysozyme was bound to phosphate sites in the surface (Bernardi and Kawasaki 1965). The enamel surface is always covered with a layer of firmly bound salivary proteins (the pellicle), which is continuously being replenished. The pellicle has a role in protecting the tooth surface, a sort of lubrication, which reduces the friction between the upper and the lower teeth, and also between the aproximal surfaces of the same jaw. This pellicle consists of minute globules which are negatively charged and consists of several salivary proteins. The chemical composition and the charge of the globules has been extensively examined: (Young, Rykke and Rölla: "On the Nature of the acquired enamel pellicle In "Tooth wear and sensitivity". (Eds) M. Addy, G. Embery, W. M-Edgar and R. Orchardson. Martinn Dunitz, London 2000 pp 29-38), and "Quantitative and qualitative analysis of human salivary micelle-like globules", Acta Odontologica Scandinavica 1999:57:105-110).

These globules are in many ways similar to the casein micelles present in milk. The pellicle can perform small maintenance jobs on the tooth surface. If a small pit occurs in the enamel surface, this pit will soon be filled with pellicle material which becomes stagnant, and later be mineralized in a few weeks time, and will then present a smooth, mineralized surface where the pit has disappeared. The pellicle material often picks up stain being deposited on the tooth surface. This stain will disappear when the pellicle is lost during wear and tear, being replenished by new pellicle material. In this way the pellicle protects the enamel against staining.

However, pellicle involved in repairing enamel scratches may well pick up stain during the mineralization process, thereby adding to the staining process. Such stain would probably be eliminated through bleaching with hydrogen peroxide. The pellicle is invisible to the naked eye, but is easily seen by scanning electron microscopy (SEM). In the oral cavity the pellicle is covered by whole saliva.

The upper four front teeth are the most visible teeth in the dentition. Here the staining is easily seen, and this area will be frequently exposed to bleaching. The location of the enamel-cementum junction on the facial aspects of the frontal aspect of these teeth is normally hidden by the gingival tissue. The area close to the frontal gingival tissue is vulnerable and should be protected, as the enamel layer is very thin at this location.

The dentin is slightly elastic, whereas the enamel is rigid. This constellation may over time, create numerous small cracks in the enamel. Such cracks can be mended by the pellicle, as described above, or filled with stained debris. Teeth can also be stained by elements such as iron and fluoride in the drinking water. The use of tetracycline during childhood may cause an intrinsic yellowish stain which is difficult to eliminate.

The present understanding of the mechanism of the development of tooth sensitivity in hydrogen peroxide bleached teeth is limited. However, it is known that the concentration of hydrogen peroxide used in professional bleaching procedures is about 30%, and whereas such concentrations have a considerable bleaching potential, they have also a high tendency to induce unfortunate side effects.

Data in the literature indicates that the density of bleached dental enamel is reduced, compared with normal enamel. This has been reported by several researchers, using different methods. A reduced density of bleached enamel was demonstrated by using micro hardness tests (R. T. Basting, A. L. Rodrigues, M. C. Serra, "The effect of seven carbamide bleaching agents on enamel micro hardness over time." J. Am. Dent Assoc. 2003; 134: 1335-1342), and by using Raman scattering and laser induced fluorescence (Jiang. T, Ma. X, Wang. Y. Sheng. X. HumHu. Y. Hu. J. "Investigation of the effects of 30% hydrogen peroxide on human tooth enamel by effects of Raman scattering and laser-induced fluorescence". J. Biomed Opt 2008, 13; 014019)

A study employing Atomic Force Microscopy detected deep grooves on the bleached surfaces, confirming loss of minerals (Turkun M et al. "Effects of 10% carbamide peroxide on the enamel surface morphology: a scanning electron microscopy study", J. Estet. Restor. Dent. 2002. 14:238-4). In an interesting histochemical study performed by Ankner et al. ("Histochemical analysis of dental hard tissues following bleaching", J. Endodontics 1998.22:28-36.) it was reported that the Ca/P ratio was reduced in bleached teeth, compared with normal teeth, indicating a selective loss of calcium, caused by to the bleaching procedure. Rotstein et al 1996, demonstrated that also dentin exhibited a reduced Ca/P ratio after bleaching. Loss of dentin after bleaching has also been reported by other authors (Tam and Noozi, "Effects of Direct and Indirect Bleach on Dentin Fractures Toughness", Journal of Dental Research. 2007; 86:1193-1197).

Mammal tissue contains peroxidase, which catalyzes the following reaction: $H_2O_2 > H_2O + O^{--}$. The $O^{--}$ is also referred to as oxygen superoxide, which is known to be an extremely reactive oxygen species which releases electrons. The superoxides are referred to as "free radicals". This reaction is easily visible and consists of an excessive amount of small bubbles of oxygen gas, leaving an aqueous phase. Tooth surfaces in the human mouth contain peroxidase located in the pellicle and in the saliva, which always covers the teeth in vivo. However, commercial bleaching agents usually contain additional peroxidase. When teeth are treated with hydrogen peroxide, oxygen superoxide is immediately released on the tooth surfaces, and chromogens causing discoloration of enamel and dentin are oxidized to invisible particles. The superoxide also oxidizes and removes the pellicle, thereby having access to the naked tooth enamel. Oxygen superoxide is a very small atom which is able to penetrate enamel and dentin, and is thereby providing a porous enamel surface with physical communication into the depth of the teeth, consisting of multiple minute canals into enamel and dentin, created by the superoxide atoms. This is shown by the experiments of Ogiwara et al. (2008), who described extensive destruction of enamel crystals during dental bleaching, including penetration of solid enamel rods.

Superoxides release electrons, and receptors of such electrons are referred to as "antioxidants". The only oxygen receptor present in the mineralized tissue in enamel is calcium ($Ca^{++}$) which lacks electrons, and thus can receive electrons emitted by the superoxide ($O^{--}$). Calcium atoms may be considered as "antioxidants". When the calcium atoms receive the electrons from the superoxide, they thereby lose their positive charges, and are therefore released and lost from the enamel crystals, which thereby suffer extensive damage as, calcium constitutes a major part of the tooth. This may well be the mechanism by which the observed selective loss of calcium during the bleaching occurs.

An important point to consider is that enamel as such, does not contain nerves, and is thus inert and unable to initiate a feeling of pain. However, dentin contains numerous nerves and nerve endings. Dentin has numerous natural microscopic tubules, running directly from the dentinal surface (which is covered by enamel or cementum), to the dental pulp. These tubules contain organic material and nerve endings which originate in the dental pulp. This contains living cells with connections to other nerve centers of the body.

It thus appears that the "pain from bleached enamel" may in fact be transmitted from nerves located in the dentin, underneath the bleached enamel. This phenomenon may in particular occur in places where the enamel is very thin, such as in the gingival frontal part of the four front teeth, as discussed previously. On such locations the superoxide can easily create direct communication between the enamel and the dentinal nerves.

It seems likely that bleaching of the dentin surface underneath the enamel can be an essential aspect of tooth bleaching. Dentin is softer than enamel and thus less resistant to the oxidation caused by the challenge of the superoxide. The yellow gray dentin may thus be bleached and the translucent enamel may then exhibit a bleached and esthetically improved dentin.

SHORT DESCRIPTION OF THE INVENTION

The present invention provides a method to reduce or eliminate dental hypersensitivity due to bleaching of teeth, by products containing hydrogen peroxide or other oxidizing agents. The bleaching process involves a selective loss of calcium, which may initiate communication between the enamel surface and the dentinal nerves as discussed above, and thereby causing hypersensitivity and pain. According to the invention the teeth are treated an aqueous solution of calcium hydroxide to replenish the observed selective loss of calcium ions, which occurs during the bleaching procedure. The method involves exposing the bleached teeth to calcium ions, preferably shortly after the bleaching is finished. The treatment with the calcium hydroxide solution should be followed by a treatment with a fluoride containing solution.

Another aspect of the invention is a kit for tooth bleaching, containing hydrogen peroxide or other oxidizing agents, and which further comprises a calcium hydroxide solution, and a fluoride containing solution in a suitable form.

FIGURES

FIG. 1: A SEM micrograph which represents a bleached human tooth showing a marked loss of mineral on a pitted enamel surface.

Figure 2:
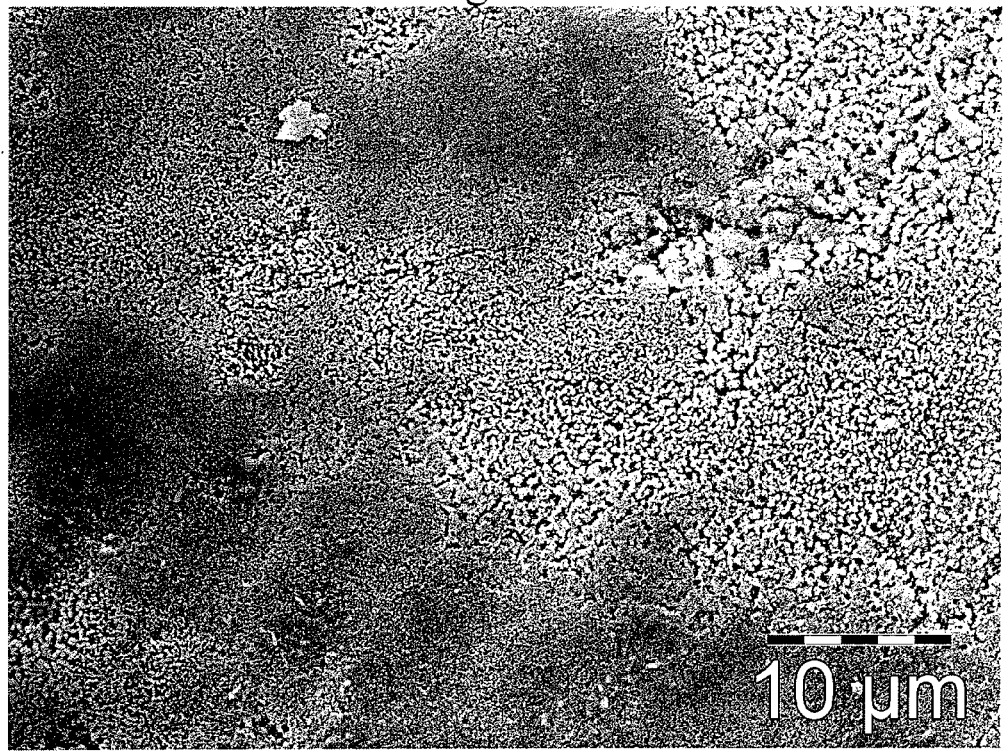

FIG. 2: A SEM micrograph showing the same tooth surface (from FIG. 1) covered with a film of dehydrated $Ca(OH)_2$.

Figure 3:
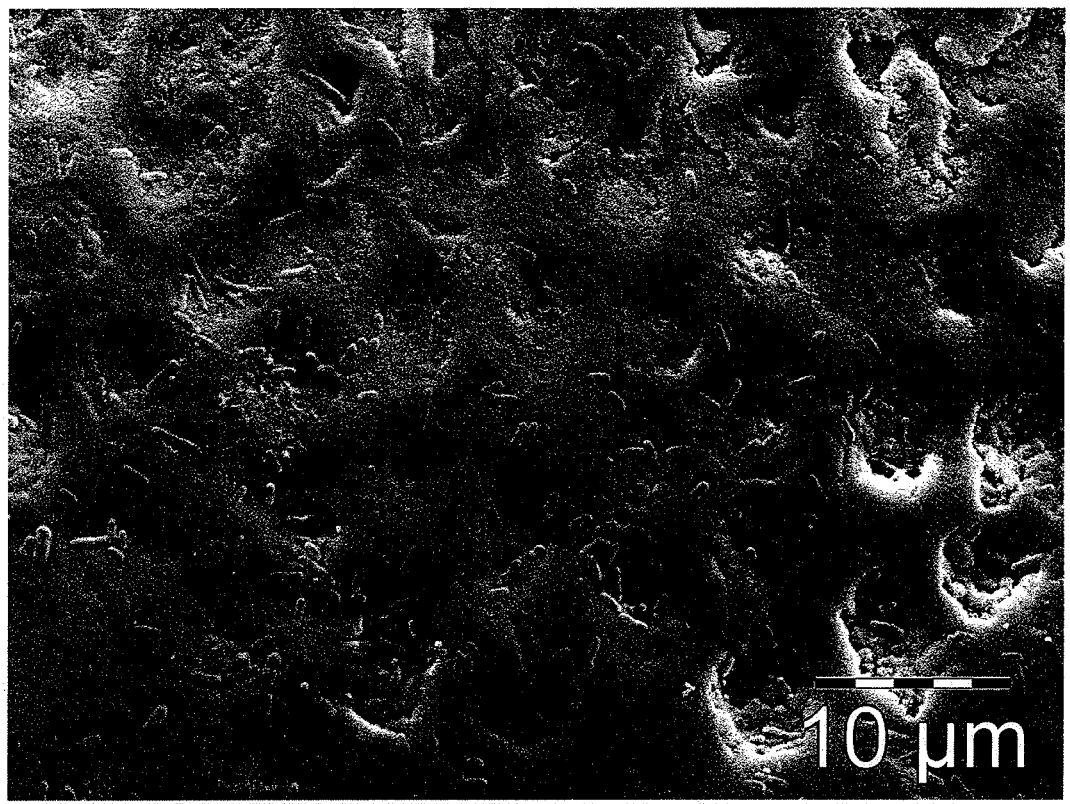

FIG. 3: A SEM micrograph showing the same tooth surface (from FIG. 2) subsequently treated with 2% by weight NaF-solution.

DETAILED DESCRIPTION OF THE INVENTION

The inventor has found that the major loss of minerals from the enamel is suffered by calcium. According to the invention this calcium is replenished to restore the original density of the enamel (and dentin), the invention thereby represents a causally based therapy. Calcium can be provided by applying an aqueous calcium hydroxide solution of suitable concentration onto the bleached and sensitized enamel. FIG. 1 above, shows a SEM micrograph of the enamel after bleaching with peroxide. As can be seen, the surface is pitted and damaged by demineralization. The loss was scarcely visible by the naked eye. Saturated, or less than saturated, aqueous solutions of $Ca(OH)_2$ exhibit a pH>10, and contain no "foreign" counter ions, which could interfere with the reactions of calcium ions with the exposed phosphate of the damaged enamel crystals. The solution of calcium hydroxide contains calcium ions and hydroxyl ions which are fully dissociated, and thus, constitutes a strong base, with a pH of 14, which provides a phosphate (−3) with very high affinity for calcium. As the calcium hydroxide solution must be able to penetrate the damaged and bleached enamel as described above, by capillary attraction to provide calcium ions, it is important that its viscosity is known to be low. Sufficient time should be allowed for the calcium treatment, at least 5 minutes, with a continuous supply of calcium, is a minimum. After this the calcium hydroxide should be allowed to dry and form a film on the damaged tooth surface. FIG. 2 shows the bleached enamel covered with a dehydrated film, which now covers the whole tooth surface. This film has a very high affinity for enamel surfaces and contains large amounts of calcium. The tooth surface is hidden behind the film. The film will penetrate and seal any communication between enamel and dentin, thus alleviating the pain from hypersensitive, bleached teeth.

It is preferred to perform a final treatment with a 2% by weight solution of NaF. FIG. 3 shows the surface after this treatment. A calcium fluoride-like mineral is formed on the tooth surface, where the calcium originates from the dehydrated film shown in FIG. 2. This process eliminates the film as such, which is calcified and represents a part of the mineralized tooth surface. It can be observed that the serious loss of mineral seen on the tooth surface in FIG. 1, has been eliminated. Only traces of the original de-mineralized areas can be seen, partly filled with calcium fluoride-like mineral which constitutes a new, mechanically strong, resistant surface. Repeated treatments with $Ca(OH)_2$ and NaF as described will further improve this surface.

Calcium hydroxide was used in dentistry in the past, in endodontic treatment, because it has an antibacterial activity due to its alkalinity. The calcium hydroxide is used in the form of a paste, consisting of dry calcium hydroxide and a small amount of fluid. Calcium serves no known purpose in endodontic treatment. Calcium hydroxide is also used in dental cements, which is assumed to protect the pulp when it happens to be exposed, during removal of carious dentin.

The present invention relates to a method to replenish the selective loss of calcium ions from the enamel, experienced during bleaching. The bleaching may cause loss of mineral which may cause communication between the enamel surface and the nerve-containing dentin thereby causing dental hypersensitivity. By providing calcium ions to the damaged, bleached surface, the communication between the inert enamel and the nerve containing dentin may be blocked, thus alleviating or eliminating the dental hypersensitivity.

The calcium hydroxide solution becomes dehydrated after some time, and forms a thin film on the bleached tooth surfaces. This film is not mechanically strong, and can also be eliminated by acidic solutions. The film, which contains calcium ions, is therefore treated with 2% by weight of NaF in an aqueous solution for at least one minute, thereby inducing deposition of calcium fluoride ($CaF_2$), of which the calcium originates from the film. The calcium fluoride creates a robust and stable tooth surface (Rölla and Saxegaard, 1990 J. dent. Res., 69; 180-85.

The method according to the invention is suited for professional operators that work from a dental surgery.

The method has been developed primarily to improve the conditions during dental bleaching, but it could also be useful in special cases where the loss of mineral is caused by other conditions than bleaching, for example by dental erosion, where the eroded surfaces often are hypersensitive and may be very painful.

EXPERIMENTAL EXAMPLE

A female volunteer of 40 years of age had performed a self-bleaching procedure on her teeth, using a home kit. She complained and described her front teeth as extremely sensitive for changes of temperature in drinks or food. The teeth were rinsed carefully with water at room temperature, and isolated with cotton rolls. The teeth were kept dry and then treated with a generous amount of a saturated aqueous solution of $Ca(OH)_2$, at an acceptable temperature, for a period of about 5 minutes. After a few additional minutes the cotton rolls were removed, and treatment with an aqueous solution of 2.0% by weight of NaF was performed, to induce formation $CaF_2$, to stabilize the calcium added. The hypersensitivity was eliminated by this brief procedure. The teeth maintained an acceptable colour, and the sensitivity has not reappeared.

The invention claimed is:

1. A method to reduce or eliminate dental hypersensitivity and loss of calcium ions caused by bleaching of tooth enamel with a product containing an oxidizing agent selected from the group consisting of hydrogen peroxide and carbamide peroxide, comprising:
    treating tooth enamel after the bleaching with an aqueous solution consisting of calcium hydroxide and water,
    wherein calcium ions of the tooth enamel lost during the bleaching process are replenished and the aqueous solution is not a paste.

2. The method of claim 1, wherein the aqueous solution consisting of calcium hydroxide and water has a pH above 10.

3. The method of claim 1, further comprising treating the tooth enamel with a fluoride containing solution after the treatment with the aqueous solution consisting of calcium hydroxide and water.

4. The method of claim 3, wherein the fluoride containing solution comprises an aqueous solution of NaF.

5. The method of claim 4, wherein the aqueous solution of NaF comprises about 2% w/w of NaF.

6. The method of claim 2, further comprising treating the tooth enamel with a fluoride containing solution after the treatment with the aqueous solution consisting of calcium hydroxide and water.

7. The method of claim 6, wherein the fluoride containing solution comprises an aqueous solution of NaF.

8. The method of claim 7, wherein the aqueous solution of NaF comprises about 2% w/w of NaF.

* * * * *